United States Patent [19]

Barton et al.

[11] 4,153,625

[45] May 8, 1979

[54] NEUTRALIZATION PROCESS

[76] Inventors: Brandon H. Barton, Cincinnati; John A. Sagel, Mt. Healthy, both of Ohio

[21] Appl. No.: 701,724

[22] Filed: Jul. 1, 1976

[51] Int. Cl.$^2$ ............................................. C07C 141/00
[52] U.S. Cl. .................. 260/457; 260/458 R; 260/459 R; 260/504 R; 260/507 R; 260/505 N; 260/513 R
[58] Field of Search ........... 260/505 E, 505 S, 505 N, 260/457, 458, 459 R, 504 R, 513 R, 507 R

[56] References Cited

U.S. PATENT DOCUMENTS 3,024,258  3/1962  Brooks et al. .......................... 260/505

OTHER PUBLICATIONS

The Merck Index, 8th ed. (1968), p. 966.

*Primary Examiner*—Alan Siegel

*Attorney, Agent, or Firm*—Richard C. Witte; Thomas H. O'Flaherty; Steven J. Goldstein

[57] ABSTRACT

This invention relates to a process for neutralizing detergent acid mixes containing unreacted sulfating agent such as sulfuric acid with an alkaline component such as sodium hydroxide. The neutralization process is highly exothermic and contains as a by-product large amounts of sodium sulfate. Due to the exothermic nature of the reaction it is necessary to use heat exchangers to regulate the temperature of the reaction mass following the addition of the alkaline component. When the sodium sulfate is supersaturated in the reaction mass, it has been observed that sulfate salts buildup upon the surfaces of the heat exchanger and eventually the system must be shut down to remove the buildup. This invention is therefore directed to a continuous neutralization and heat exchange process wherein the downtime required for removal of the sulfate salts from the heat exchanger surfaces is effectively eliminated.

23 Claims, No Drawings

NEUTRALIZATION PROCESS

BACKGROUND OF THE INVENTION

1. Field of the Invention

The invention described herein relates to a process for forming surfactants for use in detergent compositions where a step in a process includes cooling the reaction mass, following the mixture of an alkaline component, the detergent acids and excess sulfating agent.

2. Discussion of the Art

The use of anionic surfactants particularly those where the anionic character is caused by a sulfonate or a sulfate group is well known in the detergency arts. Further, the sulfation or sulfonation of precursor materials such as alkylbenzene to form alkylbenzene sulfonic acid which is subsequently neutralized to the sulfonate is also well known in the art. For instance, U.S. Pat. No. 3,024,258, issued to Brooks et al, Mar. 6, 1962, discloses a process for sulfonating a reactant continuously and rapidly as well as for separating the resulting sulfonated reactant from the excess sulfonating agent and to the continuous neutralization of the resulting detergent acids. During the neutralization step the Brooks et al patent describes cycling the neutralized product through a heat exchanger to maintain the temperature in the range of from 85° F. to 140° F. The examples of Brooks et al indicate that the final product contains sodium sulfate in water in a ratio of from about 1:11. The Brooks et al patent is herein incorpated by reference.

Similarly, other patents describing sulfonation and sulfation processes are U.S. Pat. No. 3,259,645 issued July 5, 1966, U.S. Pat. No. 3,363,994 issued Jan. 16, 1968, U.S. Pat. No. 3,350,428 issued Oct. 31, 1967, and U.S. Pat. No. 3,427, 342 issued Feb. 11, 1969, all to Brooks et al which are herein incorporated by reference. Earlier patents describing sulfonation processes include U.S. Pat. No. 2,129,826, Reilly issued Sept. 13, 1938 and U.S. Pat. No. 2,039,989, issued to Gressner May 5, 1936, both of which are herein incorporated by reference.

In the process of forming anionic surfactants which have a sulfuric or sulfonic acid moiety it is necessary to react a precursor with a sulfating agent which is a material such as sulfur trioxide to form the organic sulfuric or sulfonic acid. Materials which supply a source of sulfur trioxide for the forming of such detergent acids are known as sulfating agents and the term embraces sulfonating agents as well. Sulfating agents include pure sulfur trioxide or sulfur trioxide diluted with a gas which is inert in the reaction, such as hydrogen chloride or sulfur dioxide. The most common sulfating agent, however, is oleum which is a mixture of sulfur trioxide dissolved or suspended in sulfuric acid. The method of formation of the detergent acids, also known as the acid mix, is not material to the present invention up to the point that an excess of the sulfating agent should be present in addition to that which is required to react the detergent precursor to the desired degree of sulfation.

The reason for using an excess of the sulfating agent is basically to ensure that the detergent precursor which is a relatively expensive material will be completely reacted. That is, for ecological, product performance and cost reasons, it is undesirable to leave unreacted alkylbenzene in the detergent product as it is relatively volatile and will in the instance of spray-dried formulations be driven off upon heating.

The step following the reaction of the detergent precursor and the sulfating agent is that of neutralizing the mixture containing the organic sulfuric or sulfonic acid. This mixture will also contain the excess sulfating agent, and water which is either introduced with the reactants or formed during the sulfation reaction. This mixture is then neutralized with an alkaline component such as sodium hydroxide or sodium carbonate or a similar material to form the sodium salt of the organic sulfuric or sulfonic acid. The introduction of the alkaline component, however, also neutralizes the excess sulfating agent to form sodium sulfate.

This second mixture referred to herein as the reaction mass then contains the sodium salt of the organic sulfuric or sulfonic acid, sodium sulfate, water, and small amounts of the excess alkaline component. As the sulfation reaction and the neutralization reaction are both highly exothermic it is necessary to quench the heat of reaction to avoid bringing the reaction mass to boil as well as to avoid undesirable secondary reactions which may take place. The most common method of quenching any exothermic reaction is to pass the product of the reaction through one or more heat exchangers where excess thermal energy is removed thus lowering the temperature of the product for further processing. It is noted, that the sulfation reaction mixture may be quenched through heat exchange prior to the neutralization reaction if desired although the present invention only relates to heat exchange following the neutralization step.

The most commonly used heat exchangers for the preparation of detergents are simply a large conduit through which the reaction mass passes and a series of smaller conduits within the larger conduit through which the cooling medium flows. In operation the cooling medium is of course maintained at a temperature below that of the reaction mass which swirls around the smaller conduits. The thermal energy then flows through the walls of the smaller conduits where the heat energy is transferred to the cooling medium and removed from the system. Thus, the reaction mass is cooled to a desirable temperature for further processing.

Known systems for the neutralization step have involved processing the reaction mass in diluted form in the presence of large volumes of water. The water is present in the reaction mass from the neutralization and from the alkaline component, e.g., a solution of caustic. Water may also have been added directly to the reaction mass to purposely dilute the heat generated by the reaction.

Obvious economic reasons dictate that the presence of a large volume of water in the reaction mass is undesirable. For instance, the water present in the reaction mass must be removed if the end product is to be solid such as a spray-dried granule. Moreover, the presence of the water in the reaction mass requires that storage or processing facilities have greater volume than that required for a reaction mass with lower water content. Conversely, lowered water content in the reaction mass allows greater throughput of the final product with existing equipment.

It is also observed, aside from the advantages listed above, that other processing goals can be achieved by lowering the water content of the reaction mass. For example, sodium sulfate in dry form is usually added to the reaction mass following the heat exchange operation to aid in the preparation of granular detergent compositions. If desired, however, in the present invention the sodium sulfate may be formed in situ during the neutralization step by using excess sulfating agent over that which is needed to accomplish sulfation of the organic precursor. The excess sulfating agent is then neutralized by the alkaline component to form sodium sulfate. In the case where oleum is used as the sulfating agent versus sodium sulfate to generate a source of sodium sulfate in the product a density and cost/availability advantage favor the use of oleum. Cost and availability is of course a readily apparent advantage while the density factor allows equivalent storage facilities to hold a greater weight of oleum as opposed to dry sodium sulfate.

An additional advantage to lowering the water content of the reaction mass resides in the difference of incorporating wet versus dry silicates into the detergent compositions. Most detergent products require the presence of alkali metal silicates to provide an anti-corrosion benefit to exposed washing machine surfaces as well as to provide non-gooey granules, e.g., granules which cake or do not flow freely under humid conditions.

The silicates, as stated above, may be added to the crutcher mix containing the reaction mass as a wet or dry material. If the water content of the crutcher mix is low, as is obtained in the present invention, then a slurry of wet silicate may be added to the crutcher mix. If the water content of the crutcher is already high from the aqueous reaction mass, then it is usually necessary to add dry silicate to reduce the crutcher water content to lower the drying load when forming the crutcher mix into granules. Drying load as used above is defined as the heat energy required to remove water in granules formation. It is also observed that not withstanding the use of costly energy for drying the crutcher mix, that a point can be reached where the crutcher mix is too wet to be dried by conventional spray-drying towers such as those described in U.S. Pat. Nos. 3,629,951 and 3,629,955, both issued to R. P. Davis et al on Dec. 28, 1971, which are herein incorporated by reference.

It is thus seen that reducing the water content of the reaction mass and subsequently that of the crutcher mix is highly desirable. To effectively reduce the water content of the reaction mass it is necessary that the sodium sulfate be supersaturated in relation to the water. This is not undesirable as the sodium sulfate cannot be economically removed in a continuous detergent making operation and in any event the sodium sulfate is a very desirable ingredient, especially in its ability to act as a structurant to avoid gooey granules as previously stated in the discussion concerning the function of the silicate.

It has been observed, however, that when the reaction mass is passed through a heat exchanger with the sodium sulfate in a supersaturated condition that the heat exchanger immediately suffers a reduction in heat energy transfer capacity.

This loss of energy transfer capacity has been determined to be caused by the buildup of anhydrous sodium sulfate in the heat exchanger. Moreover, the loss of energy transfer capacity continues until the heat exchanger is completely plugged with the reaction mass. Thus, while it is extremely desirable to operate the detergent making process under conditions where the sodium sulfate is supersaturated in the reaction mass it has been impractical, if not effectively impossible, to do so.

The difficulty which the present invention alleviates is caused by the sodium sulfate which when supersaturated in the aqueous reaction mass precipitates on the surfaces of the smaller conduits in the heat exchanger and continues to precipitate until the entire heat exchanger is plugged with the precipitated sodium sulfate. At this point if there is but a single heat exchanger the neutralization reaction as well as the earlier sulfation reaction must be shutdown and the heat exchanger torn apart and cleaned or flushed with water to remove the precipitated sodium sulfate.

Alternatively, the sulfation reaction can be allowed to continue to proceed along with the neutralization reaction, however, additional capital expense is then necessary to provide a parallel series of heat exchangers through which the neutralized reaction mass is allowed to pass while the first heat exchanger has the sodium sulfate removed. Either alternative is quite costly and extremely undesirable.

A second alternative is to process the reaction mass with sufficient water present so that the sodium sulfate never becomes saturated in the reaction mass. However, such processing requires large amounts of water which, as previously discussed, is undesirable.

In view of the high degree of interest of operating heat exchangers at high capacity when removing heat from a neutralized detergent acid mix the following objects of the present invention are developed.

It is an object of the present invention to provide a method for rapidly and economically removing heat from a neutralized detergent acid mix.

It is a further object of the present invention to prepare an aqueous mixture of supersaturated sodium sulfate and the sodium salt of an organic sulfuric or sulfonic acid having as a processing step the cooling of the mixture in a heat exchanger while introducing a slurry of anhydrous sodium sulfate into the reaction mass to reduce the deposition of sodium sulfate in the heat exchanger.

Throughout the specification and claims, percentages and ratios are by weight and temperatures are in degrees Centigrade unless otherwise indicated.

SUMMARY OF THE INVENTION

In the process of removing thermal energy from an aqueous mixture of sodium sulfate and the sodium salt of an organic sulfuric or sulfonic acid or mixtures thereof the steps of:

(a) reacting the organic sulfuric or sulfonic acid and excess sulfating agent with an alkaline component thereby forming a supersaturated solution with respect to the sodium sulfate; and, (b) cooling the reaction mass formed in step (a) in a heat exchanger while introducing into the reaction mass a sufficient amount of an aqueous slurry of anhydrous sodium sulfate, to reduce the deposition of sodium sulfate on the surfaces of the heat exchanger.

DETAILED DESCRIPTION OF THE INVENTION

The present invention as stated above relates to a method of removing thermal energy from an aqueous mixture of sodium sulfate and the sodium salt of an organic sulfuric or sulfonic acid, while avoiding buildup of sodium sulfate in the heat exchanger.

In fact the present invention is advantageously utilized any time it is necessary to remove thermal energy from a supersaturated solution of sodium sulfate. Ordinarily sodium sulfate is prepared as a commercial product in the rayon making process where excess sulfuric acid is reacted with an alkaline component. Thus the present invention has utility outside of the field of detergent products and the nondetergent related aspects of the invention are employed advantageously.

For detergent products the presence of the desired level of the sodium sulfate in the end product is accomplished by over-using the sulfating agent which is present to add the anionic moiety to the detergent precursor and then neutralizing the excess sulfating agent.

For the purpose of this invention the term "detergent precursor" includes any material which following sulfation is capable of neutralization to form a surface active agent. Examples of such surface active agents are alkylbenzene sulfonates, alkyl ether sulfates, alkyl sulfates, olefin sulfonates, paraffin sulfonates, alpha-sulfocarboxylates, alpha-sulfocarboxylate alkylates, and mixtures of the foregoing. Such surfactants are listed for purposes of exemplification but the present invention is not limited to such surface active agents. Other materials which may be sulfated or sulfonated within the scope of the present invention, and embraced within the term of organic sulfuric or sulfonic acids, include toluene and benzene sulfonic acids as well as cumene sulfonic acids.

The term "sulfating agent" is interchangeable with "sulfonating agent", and examples of such materials are sulfuric acid, oleum, and chlorosulfonic acid, and sulfur trioxide. Oleum is defined as a material which is a mixture of sulfuric acid and sulfur trioxide. Oleum is the preferred sulfating agent of the present invention.

In practice the amount of the sulfating agent needed to completely sulfate the detergent precursor is greater than the actual amount of sulfating agent which is needed on a stoichiometric basis. Conveniently the actual amount of sulfating agent used is related to the spent acid strength which is defined by the following equation:

$$\% \text{ spent acid strength} = \frac{100 \text{ (moles excess } SO_3) \times \text{mol. wt. } H_2SO_4}{\text{(moles excess } SO_3 \times \text{mol. wt. } SO_3 + (H_2O)} \quad (I)$$

where (excess $SO_3$) is the sulfur trioxide introduced to the reaction over and above that used in the sulfation. This excess sulfur trioxide and the sulfuric acid present is subsequently neutralized to form sodium sulfate. The quantity ($H_2O$) is the water introduced into the system or which is present during the sulfation process. The percentage spent acid strength is a measure of the available sulfur trioxide which may be used for sulfation or sulfonation. In other words, where the sulfur trioxide would react on a one-to-one mole basis with the detergent precursor to give a sulfated product, the presence of water in the system will lower the amount of sulfur trioxide available for the sulfation of the detergent precursor. Thus, it is desirable to minimize the amount of water present during the sulfation step. The spent acid strength, as more fully described later, is preferably from about 90% to about 103%.

The second chemical reaction carried out in following the present invention is the formation of the supersaturated solution of sodium sulfate. This reaction is accomplished by neutralizing the sulfated detergent precursor and the unreacted sulfating agent with an alkaline component. The alkaline component is any material which will function as a Lewis base, e.g., a material which will take up hydrogen ions to form water. The most common alkaline components utilized in the present invention will be sodium hydroxide or sodium carbonate. Other suitable materials, however, include potassium hydroxide, potassium carbonate, and partially neutralized salts such as bicarbonates and sesquicarbonates. The first aspect of the present invention set forth in detail is the sulfation system for forming the organic sulfuric or sulfonic acid from the detergent precursor.

The Sulfation System

Sulfation or sulfonation of various organic components, when carried out with oleum or sulfuric acid, may be done on a continuous scale such as in a dominant bath system or on a single batch basis. For the purposes of the present invention, the benefits may be obtained either as single batch reaction or on a continuous process.

A. Batch System

The batch process is an operation comprising adding the sulfating agent and the organic detergent precursor which is to be sulfated or sulfonated into a vat.

The initial reaction in the batch process proceeds rapidly to completeness because of the high concentration of the reactants. However, the final concentration of the sulfated organic product in the acid mix will be lower because of the poor mixing encountered in the batch process. The yield in a batch process can, however, be increased by thoroughly mixing the system by any conventional means.

The product obtained from the batch process comprises the sulfated reaction product as well as any excess sulfating agent and unreacted detergent precursor. The resultant acid mix described above is then further processed to remove the excess sulfating agent, or the acid mix may be neutralized with the excess sulfating agent present. Preferably, the acid mix does not have the excess sulfating agent removed from it prior to neutralization, so that the sodium sulfate will be present under conditions of super-saturation in the reaction mass. The reaction mass also known as paste is transported by conventional means to the heat exchanger.

B. Dominant Bath

The dominant bath is the most commonly used oleum or sulfuric acid sulfation process. The dominant bath provides for a continuous production of an acid mix. In contrast to the batch process, the dominant bath allows the preparation of an acid mix under much more controlled reaction conditions.

In the dominant bath process the reactants are injected into a recirculating stream of reaction products. The heat of reaction which is considerable in a sulfation or sulfonation process is thus dissipated into the recirculating acid mix which facilitates heat removal and mixing. In an ideal dominant bath the reactants are completely distributed throughout the system such that all parts of the bath have an identical composition with the mean reaction time equal to the volume of the system divided by the effluent flow rate. In this context effluent is defined as the acid mix which is removed from the system to be further processed, such as paste formation. In the dominant bath system the recirculation ratio will determine the degree of approach to the ideal system. The recirculation ratio is defined as being the volume of recirculated material divided by the volume of the effluent. Typical recirculation rates which will vary according to the material to be sulfated are from 15:1 to 40:1 with an average of 25:1. Thus, a recirculation ratio of 25:1 indicates that for every part of effluent, 25 parts of acid mix are recirculated through the system. The recirculation ratio also indicates the maximum amount of new reactants which may enter the system; thus the rate at which the effluent leaves the system is equal to the rate at which the new reactants enter the system.

In contrast to a batch system where the reaction is initially fast as the reactants are high in concentration with the rate decreasing as the reactants are consumed the dominant bath provides a system where the reactants are at their final concentration and hence the reaction is relatively slower. The longer reaction time for completion of the sulfation reaction is the most notable disadvantage of the dominant bath system. The foregoing disadvantage however, is greatly outweighed by the heat removal capacity in the dominant bath resulting in less charred material.

To avoid using a dominant bath with an unduly large volume or greatly increasing the recirculation ratio, it has been suggested to remove the effluent acid mix from the system before the sulfation reaction has been completed. The effluent which has been substantially reacted is then passed through a coil of sufficient length to allow the sulfation reaction to continue to completion despite the absence of mixing. The use of the coil is possible because the effluent has been substantially reacted in the dominant bath, thus requiring little or no heat transfer in the reaction coil. The length of the coil and the recirculation ratio can thus be varied so that the various sulfatable materials can achieve maximum completeness of the reaction with the shortest period of time in the dominant bath and in the coil.

If two components are to be sulfated which require different spent acid strengths for completeness and quality, series sulfation in the dominant bath may be employed. Series sulfation is a system in which one component is first sulfated as has been previously discussed, and then that acid mix is used as a diluent for the sulfation of a second material. A common practice is to sulfonate an alkylbenzene first and then combine the acid mix with a fatty alcohol or an ethoxylated alcohol prior to sulfating the latter materials.

The acid mix, following either of the procedures described above is then converted to the paste or reaction mass as indicated under the neutralization discussion, supra.

C. Film Sulfonation

Many detergent precursors can be sulfated by using film sulfation methods. Basically the process in a film reactor comprises introducing the detergent precursor at the top of a reaction vessel such that a thin film is formed on the walls of the vessel. The film is continuously exposed to a gaseous sulfating agent as the film moves along the surface of the reaction vessel. The sulfating agent may be sulfur trioxide or sulfur trioxide diluted with a gas which is inert in the process such as sulfur dioxide.

Examples of suitable detergent precursors which may be sulfated in the film process are ethoxylated alcohols, alpha-olefins and aliphatic carboxylic acids. Further film reactor techniques are described in U.S. Pat. Nos. 3,346,505; 3,309,392; 3,531,518; and 3,535,339 herein incorporated by reference.

D. Sulfating Agent

As was previously stated in this application the term "sulfating agent" is to be used in its generic sense indicating a material which is capable of sulfating or sulfonating another compound. The sulfating agents with which the present invention is primarily concerned are sulfuric acid, oleum, chlorosulfonic acid or sulfur trioxide. The practical use of sulfuric acid as a sulfating agent is limited to those situations where 100% sulfuric acid is used, as the spent acid strength is otherwise too low to ensure sulfation of the detergent precursor. Chlorosulfonic acid is normally employed in a batch reaction while sulfur trioxide diluted with an inert gas is employed in a film reactor.

Oleum, which is a mixture of sulfuric acid and sulfur trioxide, is the preferred sulfating agent in the present invention when the sulfation is carried out in a batch process or in a dominant bath system. The acid strength of the oleum used may be as high as 65%; however, the preferred range of oleum acid strengths is between 10% and 40%. Acid strength is defined as the percentage of a mixture of sulfur trioxide and sulfuric acid which is sulfur trioxide. Thus, a 10% acid strength is 10 parts sulfur trioxide and 90 parts sulfuric acid.

The choice of the oleum strength used is dependent upon such factors as the desired degree of completeness of sulfation in the dominant bath, the limitations on heat exchanger capacity wherein higher concentrations of oleum result in substantially higher reaction temperatures, the degree of charring which can be tolerated and the choice of the material to be sulfated.

The particular materials of interest in the instant invention are alkylbenzenes, fatty alcohols and ethoxylated alcohols, although other detergent precursors are utilized in the instant invention such as alpha-olefins, fatty acids, and fatty acid esters or other sulfatable organic compounds.

As used herein the term, "sulfatable compound", is the material which when reacted with the sulfating agent will form the organic sulfuric, or sulfonic acid.

An alkylbenzene which may include some branched chain material in the alkyl group will preferentially sulfonate with sulfuric acid or oleum in the para position with minor amounts of sulfonation at other positions on the benzene ring. The sulfonation of the alkylbenzene is a nonreversible reaction; however, the presence of water in the system may reduce the spent acid strength to a point at which the sulfonation reaction does not proceed. Below a spent acid strength of about 90% the sulfonation reaction will not proceed while at spent acid concentrations above 100%, secondary reactions which affect the color of the neutralized paste and odor become troublesome. Spent acid concentrations may be from 95% to 103%, preferably in the 98.0–101% range for the best completeness of alkylbenzene sulfonation with acceptable charring. The secondary reactions which are alluded to above can include oxidation, dehydration, and rearrangement of the alkyl radical of the alkylbenzene. The apparent acid strength of the oleum used with an alkylbenzene should be from about 100% to abou 122.5%, preferably about 102% to about 122.5%. Apparent acid strength is defined as the amount of sulfuric acid which can be formed from oleum if all the sulfur trioxide is converted to sulfuric acid. Thus, by convention, a mixture of 30 parts sulfur trioxide and 70 parts sulfuric acid has an apparent acid strength of 106.75%.

The sulfonation of an alkylbenzene is preferably carried out in a dominant bath with a temperature maintained between 29° C. and 65° C., preferably from 43° C. to 55° C., with a recirculation ratio of greater than 15:1 and preferably greater than 25:1. The weight ratio of alkylbenzene to sulfating agent is from about 1:8 to 7:1, preferably about 1:4 to 10:3. Alkyl chains on an alkylbenzene contain from about 9 to 15 carbon atoms, preferably between 11 and 12 carbon atoms.

The sulfation reaction of a fatty alcohol, preferably having 10 to 20 carbon atoms, proceeds rapidly but is reversible in the presence of water. Fatty alcohols while undergoing sulfation are also prone to side reactions resulting in the formation of alkenes, ethers, esters, and aldehydes. A high spent acid strength minimizes the reversible hydrolysis but increases the dehydration and oxidation reactions noted above.

The temperature range at which sulfation of an alcohol is best accomplished in a dominant bath system is between 29° C. and 65° C., and preferably from 38° C. to 52° C. with a recirculation ratio of greater than 15:1 and preferably greater than 25:1. The apparent acid strength used in sulfating a fatty alcohol should be from about 100% to about 122.5%, preferably about 102% to about 122.5%. The spent acid strength is preferably maintained in the range of from about 90% to about 103% and preferably from about 95% to about 101%. The weight ratio of sulfating agent to fatty alcohol is from about 3:1 to about 1:4, preferably about 2:1 to about 1:2. Preferably the fatty alcohol contains from about 8 to 24 carbon atoms with especially useful materials being of the tallow length.

The sulfation of an ethoxylated alcohol may be carried out by oleum or sulfuric acid in either a batch, the dominant bath process, or by film sulfation.

The apparent acid strength used in sulfating an ethoxylated alcohol should be from about 100% to about 122.5%, preferably about 102% to about 122.5%. The sulfation of the ethoxylated alcohol may take place between about 29° C. and about 65° C. and preferably from about 40° C. to about 55° C. The percentage of spent acid strength resulting from the preparation of an alkyl ether sulfuric acid should be maintained between about 90% and about 103%, and preferably from about 95% to about 101% with a recirculation ratio of greater than 15:1, preferably greater than 25:1. The weight ratio of sulfating agent to ethoxylated alcohol is from about 7:1 to about 1:10, preferably about 3:1 to about 1:3.

The ethoxylated alcohol preferably has an alkyl radical with from 8 to 24 carbon atoms and from 1 to 30 ethoxy groups. A preferred detergent precursor is the ethoxylated alcohol with an alkyl chain length average varying between 12 and 16 carbon atoms and the average degree of ethoxylation of said mixture varying between 1 and 4 moles of ethylene oxide, said mixture comprising:

(a) from about 0% to 10% by weight of said ethoxylated alcohol mixture of compounds containing 12 or 13 carbon atoms in the alkyl radical;

(b) from about 50% to 100% by weight of said ethoxylated alcohol mixture of compounds containing 14 or 15 carbon atoms in the alkyl radical;

(c) from about 0% to 45% by weight of said ethoxylated alcohol mixture of compounds containing 16 or 17 carbon atoms in the alkyl radical;

(d) from about 0% to 10% by weight of said ethoxylated alcohol mixture of compounds containing 18 or 19 carbon atoms in the alkyl radical;

(e) from about 0% to 30% by weight of said ethoxylated alcohol mixture of compounds having a degree of ethoxylation of zero;

(f) from about 45% to 95% by weight of said ethoxylated alcohol mixture of compounds having a degree of ethoxylation of from 1 to 4;

(g) from about 5% to 25% by weight of said ethoxylated alcohol mixture of compounds having a degree of ethoxylation of from 5 to 8; and (h) from about 0% to 15% by weight of said ethoxylated alcohol mixture of compounds having a degree of ethoxylation greater than 8.

A desirable component in an acid mix containing an alkyl ether sulfuric acid or other organic sulfuric or sulfonic acid is a viscosity reducing aid such as benzoic acid. The use of benzoic acid to reduce viscosity is described in U.S. Pat. No. 3,957,671 issued May 18, 1976 to Sagel et al herein incorporated by reference. Preferably the weight ratio of the benzoic acid to the organic sulfuric or sulfonic acid is from about 1:1 to about 1:100.

Alpha-olefins having from 10 to 24 carbon atoms and fatty acids having from 8 to 20 carbon atoms and the esters of fatty acids with 1 to 14 carbon atoms in the alcohol radical may be converted to organic sulfuric or sulfonic acids and neutralized within the scope of the present invention. The acid mixes above, respectively, give upon sulfation alpha-olefin sulfonates, alpha-sulfocarboxylic acids, and esters thereof.

As used above, the esters of alpha-sulfocarboxylic acids are also known as alpha-sulfocarboxylate alkylates. An additional material which may be sulfonated and neutralized in the scope of the present invention are paraffin sulfonates having from 10 to 24 carbon atoms.

A preferred surfactant system and hence a preferred reaction mass comprises alkylbenzene sulfonate, alkyl sulfate, and alkyl ether sulfate in a respective weight ratio of about 0.5:1:2.0 to about 2.0:1:0.5. The weight ratio of the organic sulfuric or sulfonic acid to the water in the reaction mass is from about 2:1 to about 1:2, preferably about 10:16 to about 1:1.

E. Neutralization Step

Detergent compositions are ordinarily sold as solid materials and as such it is necessary to convert the organic sulfuric or sulfonic acid, which is a viscous liquid, into a fully or partially neutralized salt. The neutralization may be accomplished by suitable alkaline components as previously stated, which include sodium carbonate, sodium hydroxide, and the acid salts of carbonates such as bicarbonates and sesquicarbonates. The aforementioned components are merely those which are conveniently used, and in fact, any sodium containing Lewis base may be used. It is further noted that other non-sodium Lewis bases may be employed with the sodium containing Lewis base. It is preferred as stated above, that the reaction mass in the claimed process should contain the sodium sulfate at supersaturation following the neutralization step. This, or course, means that during the removal of thermal energy following neutralization that the sodium sulfate will be supersaturated within the heat exchanger(s). The pH of the reaction mass is conveniently from about 6 to about 12.

Subsequent to the neutralization process, the aqueous mixture containing the neutralized organic sulfuric or sulfonic acid, the sodium sulfate, small amounts of the alkaline component, will be passed through one or more heat exchangers to lower the temperature of the reaction mass also known as the paste.

It is also often desirable to recirculate a portion of the neutralized paste. The unneutralized acid mix is added to the recirculating paste stream to dilute the acid mix and further control the temperature upon neutralization. This operation is known as paste recirculation and avoids diluting the acid mix with components which are undesirable in the final product, e.g., water. The paste recirculation ratio is more preferably greater than 5:1, and most preferably greater than 10:1 of parts paste per part acid mix. The portion of the neutralized paste, which is not recycled, is drawn off for further processing into the detergent composition.

It was noted above that any of several conventional heat exchangers may be used with the present invention. Most commonly, however, the type of heat exchanger which will be used in the present invention, is a large conduit through which the aqueous mixture containing supersaturated sodium sulfate passes, preferably with turbulence to facilitate mixing. Inside the large conduit are one or more smaller conduits through which the cooling medium flows. Suitable heat exchangers as previously stated are manufactured by American Standard of Buffalo, N.Y. 14240. Such devices are discussed in detail in American Standard Bulletin 104-24 5M 7-72KC, herein incorporated by reference.

The most convenient cooling medium will of course be water at the required temperature. However, any cooling medium any be used provided that it can rapidly remove heat from the paste stream flowing through the larger conduit. It is preferred, but not necessary, that the flow rate of the cooling medium as it passes through the smaller conduit is sufficient to accomplish turbulent flow to minimize the amount of coolant which is required per given quantity of paste. This minimizes not only the amount of cooling medium which must be used, but also the amount of space which must be taken up within the larger conduit by the smaller conduits containing the cooling medium. The walls of the smaller conduit by convention are constructed to rapidly transfer heat from the reaction mass to the cooling medium. The heat exchanger will be run such that the cooling medium therein is maintained between about 5° C. and 100° C., preferably about 10° C. to about 70° C., more preferably between about 30° C. and about 65° C. As the object of utilizing the heat exchanger(s) is to remove thermal energy from the reaction mass, it is preferred that the temperature of the reaction mass, as it exists from the last heat exchanger in the series be in the range of about 100° C. to about 50° C., preferably about 95° C. to about 60° C.

F. Slurry Introduction

The present invention accomplishes the reduction of sodium sulfate precipitation in the heat exchanger by, surprisingly enough, increasing the amount of sodium sulfate within the heat exchanger. That is, it is not the amount of sodium sulfate which is present in the heat exchanger but rather the form of the sulfate which is important.

While not wishing to be bound by any particular theory, it is believed that the discovery of the property of controlled crystal growth accounts for the present invention. That is, as the sodium sulfate is supersaturated, almost any disturbance within the reaction mass will cause the sodium sulfate to precipitate out. Unfortunately, sodium sulfate in its anhydrous form plates out on the surfaces within the heat exchanger. Eventually if nothing is done to counteract the plating out, the system will become completely plugged with the sodium sulfate. It has been discovered, however, that if a slurry of anhydrous sodium sulfate is introduced into the aqueous mixture in the heat exchanger, that the system may be operated continuously without the need to shutdown the heat exchanger.

Thus, if a sufficient amount of a supersaturated anhydrous sodium sulfate slurry is introduced into the aqueous mixture the precipitation of sodium sulfate on heat exchanger surfaces is diminished. Preferably the weight ratio of the slurry to the aqueous mixture is from about 2:1 to about 1:200. The anhydrous sodium sulfate in the slurry preferably have a particle size of 0.01 micron to 100 microns, more preferably 0.03 micron to 20 microns. The anhydrous sodium sulfate is preferably present in a ratio to the water in the slurry of from about 160:100 to about 42:100. The slurry is introduced into the aqueous mixture by any convenient means. It is preferred that the slurry be introduced into the recirculation loop as previously described to give maximum effectiveness. The slurry is conveniently delivered to the heat exchanger through the means described in U.S. Pat. Nos. 2,825,543 and 2,987,380 issued Mar. 4, 1958 and June 6, 1961 to McCracken et al and Brumbaugh et al respectively, both of which are incorporated herein by reference.

It is believed that in the present system that by introducing the slurry of anhydrous sodium sulfate into the aqueous mixture that the precipitating anhydrous sodium will not deposit onto the conduit containing the cooling medium. Rather, the sulfate in the slurry seeds the precipitation of the sodium sulfate in the aqueous mixture and the precipitated sodium sulfate is carried out of the heat exchanger with the remainder of the reaction mass. The predominant salt which would otherwise precipitate is anhydrous sodium sulfate, thus the slurry accomplishes homogeneous seeding in the aqueous mixture. The positive effect of the present invention is two-fold. First, the aqueous mixture is run under conditions of supersaturation and second, the amount of sodium sulfate is further increased by the introduction of the sulfate in the slurry. An additional benefit to using the anhydrous sodium sulfate slurry is that it will function as a heat sink provided that the temperature of the slurry is less than that of the aqueous mixture.

To maintain the maximum efficiency of the present system, as well as to ensure that the maximum amount of sodium sulfate is in the end product, it is desirable that the weight ratio of the sodium sulfate to the water in the paste or reaction mass within the heat exchanger should be from about 100:60, to about 42:100, most preferably from about 40:30 to about 45:100. The water content is more fully defined as the total water free or bound within the system.

The following are examples of the present invention:

EXAMPLE I

A detergent acid mix is prepared with oleum having an acid strength of 106.75%. The acid mix with excess sulfuric acid present is then neutralized with aqueous sodium hydroxide solution to give a paste (reaction mass) comprising in parts:
7.0—sodium dodecyl benzene sulfonate
5.5—sodium hexadecyl triethoxy sulfate
5.5—sodium tallow sulfate 12.0—sodium sulfate
23.0—water
trace—free sulfur trioxide
trace—free caustic The paste which is at a temperature of about 65° C. is then introduced into an American Standard SSCF two pass heat exchanger, model number 06800. The paste flows through the heat exchanger under conditions of turbulent flow.

An aqueous slurry of anhydrous sodium sulfate comprising 45 parts of the salt to 100 parts water is introduced into the aqueous mixture (paste) in a ratio of the slurry to the aqueous mixture of 1:10.

The cooling medium in the heat exchanger is water which enters the heat exchanger at about 29° C. and exits at about 34° C. The velocity of the water is such that turbulent flow occurs in the heat exchanger.

When operating under the conditions above the heat exchanger requires only routine maintenance. In contrast, an identical system operated at the same cooling medium temperature range without the benefit of the slurry introduction into the aqueous mixture will lose substantial heat transfer and paste flow capability in about ½ hour and will require a shutdown to remove the accumulated sodium sulfate within about 3 hours.

EXAMPLE II

Example I is repeated using as parts of paste to be cooled
17—sodium dodecyl benzene sulfonate or
17—sodium tallow alcohol sulfate
14—sodium sulfate
22—water
trace—free sulfur trioxide
trace—free caustic Substantially similar results to those of Example I are obtained. Further, similar results are obtained when the above example is modified to a surfactant system containing 18 parts, 16 of which are sodium hexadecyl triethoxy sulfate and 2 parts tallow alcohol sulfate.

EXAMPLE III

Sulfuric acid which is 85% active (15% H₂O) is completely neutralized with dry sodium hydroxide. The reaction mass is then passed through a heat exchanger as defined in Example I. A slurry of anhydrous sodium sulfate as defined in Example I is introduced into the heat exchanger to promote crystal growth on the anhydrous sodium sulfate. The cooling medium (water) in the heat exchanger is maintained at 38° C. and the reaction mass is cooled from 95° C. to 90° C. As a comparative example the same system without the slurry introduction becomes plugged with sodium sulfate.

What is claimed is:

1. In the process of nuetralizing an organic sulfuric or sulfonic acid or mixtures thereof in the presence of excess sulf(on)ating agent the steps of:
   (a) reacting said organic sulfuric or sulfonic acid and excess sulf(on)ating agent with a sodium alkaline component thereby forming a supersaturated solution with respect to the sodium sulfate formed during said reaction; and,
   (b) cooling the reaction mass formed in step (a) in a heat exchanger while introducing into the reaction mass an amount of an aqueous slurry of anhydrous sodium sulfate, said amount of sodium sulfate being sufficient to reduce the deposition of sodium sulfate on the surfaces of the heat exchanger.

2. The process of claim 1 wherein the cooling medium is maintained between 5° C. and 100° C.

3. The process of claim 1 wherein the weight ratio of the anhydrous sodium sulfate to the water in the aqueous slurry is from about 160:100 to about 42:100.

4. The process of claim 1 wherein the organic sulfuric or sulfonic acid is selected from the group consisting of alkylbenzene sulfonic acid, alkyl sulfuric acid, alkyl ether sulfuric acid, olefin sulfonic acid, alkyl sulfonic acid, alpha-sulfocarboxylic acid, alpha-sulfocarboxylic acid alkylates, and mixtures thereof.

5. The process of claim 1 wherein the weight ratio of the aqueous slurry to the aqueous mixture is from about 2:1 to about 1:200.

6. The process of claim 1 wherein the reaction mass is further cooled by one or more additional heat exchangers.

7. The process of claim 1 wherein the cooling medium is water maintained at a temperature of from about 10° C. to about 70° C.

8. The process of claim 1 wherein the aqueous mixture contains benzoic acid in an amount sufficient to reduce the viscosity of the aqueous mixture.

9. The process of claim 8 wherein the benzoic acid has an alkali metal cation and is present in a weight ratio to the organic sulfuric or sulfonic acid of from about 1:1 to abut 1:100.

10. The process of claim 1 wherein the reaction mass formed in step (a) is cooled to from about 100° C. to about 50° C. by the heat exchanger.

11. The process of claim 4 wherein the organic sulfuric or sulfonic acid is selected from the group consisting of alkylbenzene sulfuric acid, alkyl sulfuric acid, and alkyl ether sulfuric acid and mixtures thereof.

12. The process of claim 11 wherein the organic sulfuric or sulfonic acid is an alkylbenzene sulfonic acid.

13. The process of claim 11 wherein the organic sulfuric or sulfonic acid is an alkyl sulfuric acid.

14. The process of claim 11 wherein the organic sulfuric or sulfonic acid is an alkyl ether sulfuric acid.

15. The process of claim 1 wherein the alkaline component is selected from the group consisting of the sodium hydroxide, sodium carbonate, sodium bicarbonate, sodium sesquicarbonate and mixtures thereof.

16. In the process of nuetralizing an organic sulfuric or sulfonic acid selected from the group consisting of alkylbenzene sulfonic acids, alkyl sulfuric acids, and alkyl ether sulfuric acids and mixtures thereof in the presence of excess sulf(on)ating agent, the steps of:
   (a) reacting the organic sulfuric or sulfonic acid and excess sulf(on)ating agent with an alkaline component selected from the group consisting of sodium hydroxide, sodium carbonate, sodium bicarbonate, and sodium sesquicarbonate and mixtures thereof, thereby forming a supersaturated solution with respect to the sodium sulfate formed during said reaction; and
   (b) cooling the reaction mass formed in step (a) in a heat exchanger while introducing into the reaction mass an amount of an aqueous slurry of anhydrous sodium sulfate, said amount of sodium sulfate being sufficient to reduce the deposition of sodium sulfate on the surfaces of the heat exchanger.

17. The process of claim 16 wherein the sodium salt of the organic sulfuric or sulfonic acid is an alkylbenzene sulfonic acid.

18. The process of claim 16 wherein the sodium salt of the organic sulfuric or sulfonic acid is an alkyl sulfuric acid.

19. The process of claim 16 wherein the sodium salt of the organic sulfuric or sulfonic acid is an alkyl ether sulfuric acid.

20. The process of claim 16 wherein the weight ratio of the anhydrous sodium sulfate to the water in the aqueous slurry is from about 160:100 to about 42:100.

21. The process of claim 20 wherein the weight ratio of the aqueous slurry to the aqueous mixture is from about 2:1 to about 1:200.

22. The process of claim 21 wherein the sodium salt of the organic sulfuric or sulfonic acid is a mixture comprising the sodium salts of an alkylbenzene sulfonic acid, an alkyl sulfuric acid and an alkyl ether sulfuric acid present in a weight ratio of from about 0.5:1.0:2.0 to about 2.0:1.0:0.5 and wherein the sodium salt of the organic sulfuric and sulfonic acid is present in a weight ratio to the water in the reaction mass of from about 10:16 to about 1:1 by weight.

23. The process of claim 22 wherein the temperature of the cooling medium is water maintained at from about 5° C. to about 100° C.

* * * * *